(12) United States Patent
Rabinowitz

(10) Patent No.: US 7,488,469 B2
(45) Date of Patent: *Feb. 10, 2009

(54) DELIVERY OF CAFFEINE THROUGH AN INHALATION ROUTE

(75) Inventor: Joshua D Rabinowitz, Princeton, NJ (US)

(73) Assignee: Alexza Pharmaceuticals, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/488,302

(22) Filed: Jul. 18, 2006

(65) Prior Publication Data

US 2006/0257328 A1 Nov. 16, 2006

Related U.S. Application Data

(63) Continuation of application No. 10/302,010, filed on Nov. 21, 2002, now Pat. No. 7,078,016.

(60) Provisional application No. 60/332,279, filed on Nov. 21, 2001.

(51) Int. Cl.
*A61K 9/12* (2006.01)
*A61K 9/14* (2006.01)
*A61M 15/00* (2006.01)

(52) U.S. Cl. ............................ 424/45; 424/46; 424/434; 424/489; 424/499; 514/958; 128/200.14; 128/200.15; 128/200.24

(58) Field of Classification Search .................... 424/45, 424/46, 434, 489, 499; 514/958; 218/200.14, 218/200.24, 203.15
See application file for complete search history.

(56) References Cited

U.S. PATENT DOCUMENTS

| | | | |
|---|---|---|---|
| 3,560,607 A | 2/1971 | Hartley et al. | |
| 3,949,743 A | 4/1976 | Shanbrom | |
| 3,982,095 A | 9/1976 | Robinson | |
| RE30,285 E | 5/1980 | Babington | |
| 4,303,083 A | 12/1981 | Burruss, Jr. | |
| 4,484,576 A | 11/1984 | Albarda | |
| 4,566,451 A | 1/1986 | Badewien | |
| 4,734,560 A | 3/1988 | Bowen | |
| 4,735,217 A | 4/1988 | Gerth et al. | |
| 4,853,517 A | 8/1989 | Bowen et al. | |
| 4,895,719 A | 1/1990 | Radhakrishnun et al. | |
| 4,906,417 A | 3/1990 | Gentry | |
| 4,917,119 A | 4/1990 | Potter et al. | |
| 4,941,483 A | 7/1990 | Ridings et al. | |
| 5,049,389 A | 9/1991 | Radhakrishnun | |
| 5,099,861 A | 3/1992 | Clearman et al. | |
| 5,146,915 A | 9/1992 | Montgomery | |
| 5,366,770 A | 11/1994 | Wang | |
| 5,388,574 A * | 2/1995 | Ingebrethsen | 128/203.17 |
| 5,456,247 A | 10/1995 | Shilling et al. | |
| 5,456,677 A * | 10/1995 | Spector | 604/290 |
| 5,525,329 A | 6/1996 | Snyder et al. | |
| 5,544,646 A | 8/1996 | Lloyd et al. | |
| 5,592,934 A | 1/1997 | Thwaites | |
| 5,605,146 A | 2/1997 | Sarela | |
| 5,649,554 A | 7/1997 | Sprinkel et al. | |
| 5,694,919 A | 12/1997 | Rubsamen et al. | |
| 5,735,263 A | 4/1998 | Rubsamen et al. | |
| 5,738,865 A | 4/1998 | Baichwal et al. | |
| 5,743,251 A | 4/1998 | Howell et al. | |
| 5,758,637 A | 6/1998 | Ivri et al. | |
| 5,840,246 A | 11/1998 | Hammons et al. | |
| 5,874,481 A | 2/1999 | Weers et al. | |
| 5,894,841 A | 4/1999 | Voges | |
| 5,900,416 A * | 5/1999 | Markson | 424/728 |
| 5,915,378 A | 6/1999 | Lloyd et al. | |
| 5,918,595 A | 7/1999 | Olsson et al. | |
| 5,934,272 A | 8/1999 | Lloyd et al. | |

(Continued)

FOREIGN PATENT DOCUMENTS

EP 0 358 114 3/1990

(Continued)

OTHER PUBLICATIONS

U.S. Appl. No. 11/687,466, filed Mar. 16, 2007, Zaffaroni et al.

(Continued)

*Primary Examiner*—Mina Haghighatian
(74) *Attorney, Agent, or Firm*—Swanson & Bratschun, L.L.C.

(57) ABSTRACT

The present invention relates to the delivery of caffeine through an inhalation route. Specifically, it relates to aerosols containing caffeine that are used in inhalation therapy. In a composition aspect of the present invention, the aerosol comprises particles comprising at least 5 percent by weight of caffeine. In a method aspect of the present invention, caffeine is delivered to a mammal through an inhalation route. The method comprises: a) heating a composition, wherein the composition comprises at least 5 percent by weight of caffeine, to form a vapor; and, b) allowing the vapor to cool, thereby forming a condensation aerosol comprising particles, which is inhaled by the mammal. In a kit aspect of the present invention, a kit for delivering caffeine through an inhalation route to a mammal is provided which comprises: a) a composition comprising at least 5 percent by weight of caffeine; and, b) a device that forms a caffeine containing aerosol from the composition, for inhalation by the mammal.

17 Claims, 1 Drawing Sheet

U.S. PATENT DOCUMENTS

| | | | |
|---|---|---|---|
| 5,957,124 A | 9/1999 | Lloyd et al. | |
| 5,960,792 A | 10/1999 | Lloyd et al. | |
| 5,993,805 A | 11/1999 | Sutton et al. | |
| 6,041,777 A * | 3/2000 | Faithfull et al. | 128/200.24 |
| 6,051,566 A | 4/2000 | Bianco | |
| 6,089,857 A | 7/2000 | Matsuura et al. | |
| 6,090,212 A | 7/2000 | Mahawili | |
| 6,095,134 A * | 8/2000 | Sievers et al. | 128/200.14 |
| 6,095,153 A | 8/2000 | Kessler et al. | |
| 6,102,036 A | 8/2000 | Slutsky et al. | |
| 6,125,853 A | 10/2000 | Susa et al. | |
| 6,241,969 B1 | 6/2001 | Saidi et al. | |
| 6,255,334 B1 | 7/2001 | Sands | |
| 6,403,597 B1 | 6/2002 | Wilson et al. | |
| 6,461,591 B1 | 10/2002 | Keller et al. | |
| 6,506,762 B1 | 1/2003 | Horvath et al. | |
| 6,514,482 B1 * | 2/2003 | Bartus et al. | 424/45 |
| 6,591,839 B2 | 7/2003 | Meyer et al. | |
| 6,613,308 B2 | 9/2003 | Bartus et al. | |
| 6,632,047 B2 | 10/2003 | Vinegar et al. | |
| 6,682,716 B2 | 1/2004 | Hodges et al. | |
| 6,694,975 B2 | 2/2004 | Schuster et al. | |
| 6,716,415 B2 | 4/2004 | Rabinowitz et al. | |
| 6,716,416 B2 | 4/2004 | Rabinowitz et al. | |
| 6,716,417 B2 | 4/2004 | Rabinowitz et al. | |
| 6,737,042 B2 | 5/2004 | Rabinowitz et al. | |
| 6,737,043 B2 | 5/2004 | Rabinowitz et al. | |
| 6,740,307 B2 | 5/2004 | Rabinowitz et al. | |
| 6,740,308 B2 | 5/2004 | Rabinowitz et al. | |
| 6,740,309 B2 | 5/2004 | Rabinowitz et al. | |
| 6,743,415 B2 | 6/2004 | Rabinowitz et al. | |
| 6,759,029 B2 | 7/2004 | Hale et al. | |
| 6,776,978 B2 | 8/2004 | Rabinowitz et al. | |
| 6,780,399 B2 | 8/2004 | Rabinowitz et al. | |
| 6,780,400 B2 | 8/2004 | Rabinowitz et al. | |
| 6,783,753 B2 | 8/2004 | Rabinowitz et al. | |
| 6,797,259 B2 | 9/2004 | Rabinowitz et al. | |
| 6,803,031 B2 | 10/2004 | Rabinowitz et al. | |
| 6,805,853 B2 | 10/2004 | Rabinowitz et al. | |
| 6,805,854 B2 | 10/2004 | Hale et al. | |
| 6,814,954 B2 | 11/2004 | Rabinowitz et al. | |
| 6,814,955 B2 | 11/2004 | Rabinowitz et al. | |
| 6,855,310 B2 | 2/2005 | Rabinowitz et al. | |
| 6,884,408 B2 | 4/2005 | Rabinowitz et al. | |
| 6,994,843 B2 | 2/2006 | Rabinowitz et al. | |
| 7,005,121 B2 | 2/2006 | Rabinowitz et al. | |
| 7,005,122 B2 | 2/2006 | Hale et al. | |
| 7,008,615 B2 | 3/2006 | Rabinowitz et al. | |
| 7,008,616 B2 | 3/2006 | Rabinowitz et al. | |
| 7,011,819 B2 | 3/2006 | Hale et al. | |
| 7,011,820 B2 | 3/2006 | Rabinowitz et al. | |
| 7,014,840 B2 | 3/2006 | Hale et al. | |
| 7,014,841 B2 | 3/2006 | Rabinowitz et al. | |
| 7,018,619 B2 | 3/2006 | Rabinowitz et al. | |
| 7,018,620 B2 | 3/2006 | Rabinowitz et al. | |
| 7,018,621 B2 | 3/2006 | Hale et al. | |
| 7,022,312 B2 | 4/2006 | Rabinowitz et al. | |
| 7,029,658 B2 | 4/2006 | Rabinowitz et al. | |
| 7,033,575 B2 | 4/2006 | Rabinowitz et al. | |
| 7,045,118 B2 | 5/2006 | Rabinowitz et al. | |
| 7,045,119 B2 | 5/2006 | Rabinowitz et al. | |
| 7,048,909 B2 | 5/2006 | Rabinowitz et al. | |
| 7,052,679 B2 | 5/2006 | Rabinowitz et al. | |
| 7,052,680 B2 | 5/2006 | Rabinowitz et al. | |
| 7,060,254 B2 | 6/2006 | Rabinowitz et al. | |
| 7,060,255 B2 | 6/2006 | Rabinowitz et al. | |
| 7,063,830 B2 | 6/2006 | Rabinowitz et al. | |
| 7,063,831 B2 | 6/2006 | Rabinowitz et al. | |
| 7,063,832 B2 | 6/2006 | Rabinowitz et al. | |
| 7,067,114 B2 | 6/2006 | Rabinowitz et al. | |
| 7,070,761 B2 | 7/2006 | Rabinowitz et al. | |
| 7,070,762 B2 | 7/2006 | Rabinowitz et al. | |
| 7,070,763 B2 | 7/2006 | Rabinowitz et al. | |
| 7,070,764 B2 | 7/2006 | Rabinowitz et al. | |
| 7,070,765 B2 | 7/2006 | Rabinowitz et al. | |
| 7,070,766 B2 | 7/2006 | Rabinowitz et al. | |
| 7,078,016 B2 | 7/2006 | Rabinowitz et al. | |
| 7,078,017 B2 | 7/2006 | Rabinowitz et al. | |
| 7,078,018 B2 | 7/2006 | Rabinowitz et al. | |
| 7,078,019 B2 | 7/2006 | Rabinowitz et al. | |
| 7,078,020 B2 | 7/2006 | Rabinowitz et al. | |
| 7,087,216 B2 | 8/2006 | Rabinowitz et al. | |
| 7,087,217 B2 | 8/2006 | Rabinowitz et al. | |
| 7,087,218 B2 | 8/2006 | Rabinowitz et al. | |
| 7,089,934 B2 | 8/2006 | Staniforth et al. | |
| 7,090,830 B2 | 8/2006 | Hale et al. | |
| 7,094,392 B2 | 8/2006 | Rabinowitz et al. | |
| 7,108,847 B2 | 9/2006 | Rabinowitz et al. | |
| 7,115,250 B2 | 10/2006 | Rabinowitz et al. | |
| 7,169,378 B2 | 1/2007 | Rabinowitz et al. | |
| 2002/0086852 A1 | 7/2002 | Cantor | |
| 2002/0176841 A1 | 11/2002 | Barker et al. | |
| 2003/0004142 A1 | 1/2003 | Prior et al. | |
| 2003/0015196 A1 | 1/2003 | Hodges et al. | |
| 2003/0015197 A1 | 1/2003 | Hale et al. | |
| 2003/0032638 A1 | 2/2003 | Kim et al. | |
| 2003/0051728 A1 | 3/2003 | Lloyd et al. | |
| 2003/0062042 A1 | 4/2003 | Wensley et al. | |
| 2003/0118512 A1 | 6/2003 | Shen | |
| 2003/0131843 A1 | 7/2003 | Lu | |
| 2003/0138508 A1 | 7/2003 | Novack et al. | |
| 2003/0209240 A1 | 11/2003 | Hale et al. | |
| 2004/0009128 A1 | 1/2004 | Rabinowitz et al. | |
| 2004/0096402 A1 | 5/2004 | Hodges et al. | |
| 2004/0099266 A1 | 5/2004 | Cross et al. | |
| 2004/0101481 A1 | 5/2004 | Hale et al. | |
| 2004/0102434 A1 | 5/2004 | Hale et al. | |
| 2004/0105818 A1 | 6/2004 | Every et al. | |
| 2004/0105819 A1 | 6/2004 | Hale et al. | |
| 2004/0234699 A1 | 11/2004 | Hale et al. | |
| 2004/0234914 A1 | 11/2004 | Hale et al. | |
| 2004/0234916 A1 | 11/2004 | Hale et al. | |
| 2005/0034723 A1 | 2/2005 | Bennett et al. | |
| 2005/0037506 A1 | 2/2005 | Hale et al. | |
| 2005/0079166 A1 | 4/2005 | Damani et al. | |
| 2005/0126562 A1 | 6/2005 | Rabinowitz et al. | |
| 2005/0131739 A1 | 6/2005 | Rabinowitz et al. | |
| 2005/0258159 A1 | 11/2005 | Hale et al. | |
| 2005/0268911 A1 | 12/2005 | Cross et al. | |
| 2006/0032496 A1 | 2/2006 | Hale et al. | |
| 2006/0032501 A1 | 2/2006 | Hale et al. | |
| 2006/0120962 A1 | 6/2006 | Rabinowitz et al. | |
| 2006/0153779 A1 | 7/2006 | Rabinowitz et al. | |
| 2006/0177382 A1 | 8/2006 | Rabinowitz et al. | |
| 2006/0193788 A1 | 8/2006 | Hale et al. | |
| 2006/0216243 A1 | 9/2006 | Rabinowitz et al. | |
| 2006/0216244 A1 | 9/2006 | Rabinowitz et al. | |
| 2006/0233717 A1 | 10/2006 | Hale et al. | |
| 2006/0233718 A1 | 10/2006 | Rabinowitz et al. | |
| 2006/0233719 A1 | 10/2006 | Rabinowitz et al. | |
| 2006/0239936 A1 | 10/2006 | Rabinowitz et al. | |
| 2006/0246011 A1 | 11/2006 | Rabinowitz et al. | |
| 2006/0246012 A1 | 11/2006 | Rabinowitz et al. | |
| 2006/0251587 A1 | 11/2006 | Rabinowitz et al. | |
| 2006/0257328 A1 | 11/2006 | Rabinowitz et al. | |
| 2006/0257329 A1 | 11/2006 | Rabinowitz et al. | |
| 2006/0269486 A1 | 11/2006 | Rabinowitz et al. | |
| 2006/0269487 A1 | 11/2006 | Rabinowitz et al. | |
| 2006/0280692 A1 | 12/2006 | Rabinowitz et al. | |
| 2006/0286042 A1 | 12/2006 | Rabinowitz et al. | |
| 2006/0286043 A1 | 12/2006 | Rabinowitz et al. | |
| 2007/0014737 A1 | 1/2007 | Rabinowitz et al. | |
| 2007/0028916 A1 | 2/2007 | Hale et al. | |
| 2007/0031340 A1 | 2/2007 | Hale et al. | |

| 2007/0122353 | A1 | 5/2007 | Hale et al. |
| 2007/0140982 | A1 | 6/2007 | Every et al. |
| 2007/0178052 | A1 | 8/2007 | Rabinowitz et al. |
| 2007/0286816 | A1 | 12/2007 | Hale et al. |

FOREIGN PATENT DOCUMENTS

| EP | 0 606 486 | 7/1994 |
| EP | 1 080 720 | 3/2001 |
| GB | 903866 | 8/1962 |
| WO | WO 91/07947 | 6/1991 |
| WO | WO 94/09842 | 5/1994 |
| WO | WO 96/00071 | 1/1996 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 97/27804 | 8/1997 |
| WO | WO 98/22170 | 5/1998 |
| WO | WO 98/31346 | 7/1998 |
| WO | WO 98/36651 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/27363 | 5/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 01/13957 | 3/2001 |
| WO | WO 01/41732 | 6/2001 |
| WO | WO 01/80829 | 11/2001 |
| WO | WO 02/24158 | 3/2002 |

OTHER PUBLICATIONS

Office Action mailed Dec. 4, 2003 with respect to U.S. Appl. No. 10/057,198.
Office Action mailed Sep. 20, 2005 with respect to U.S. Appl. No. 10/057,198.
Office Action mailed Jul. 3, 2006 with respect to U.S. Appl. No. 10/057,198.
Office Action mailed Jan. 26, 2007 with respect to U.S. Appl. No. 10/057,198.
Office Action mailed Dec. 15, 2003 with respect to U.S. Appl. No. 10/057,197.
Office Action mailed Jun. 3, 2004 with respect to U.S. Appl. No. 10/057,197.
Office Action mailed Jan. 12, 2005 with respect to U.S. Appl. No. 10/057,197.
Office Action mailed Sep. 21, 2006 with respect to U.S. Appl. No. 10/057,197.
Office Action mailed Feb. 27, 2004 with respect to U.S. Appl. No. 10/146,080.
Office Action mailed Aug. 25, 2005 with respect to U.S. Appl. No. 10/146,080.
Office Action mailed Jun. 5, 2006 with respect to U.S. Appl. No. 10/146,080.
Office Action mailed Mar. 20, 2007 with respect to U.S. Appl. No. 10/146,080.
Office Action mailed Aug. 13, 2003 with respect to U.S. Appl. No. 10/153,313.
Bennett, R. L. et al. (1981). "Patient-Controlled Analgesia: A New Concept of Postoperative Pain Relief," Annual Surg. 195(6):700-705.
Carroll, M.E. et al. (1990), "Cocaine-Base Smoking in Rhesus Monkey: Reinforcing and Physiological Effects," Psychopharmacology (Berl) 102:443-450.
Clark, A. and Byron, P. (1986). "Dependence of Pulmonary Absorption Kinetics on Aerosol Particle Size," Z. Erkrank. 166:13-24.
Darquenne, C. et al. (1997). "Aerosol Dispersion in Human Lung: Comparison Between Numerical Simulations and Experiments for Bolus Tests," American Physiological Society. 966-974.
Database WPI, Section CH, Week 198941, Derwent Publications Ltd., London, GB; AN 1989-297792, AP002230849 & JP 01 221313 (Nippon Create KK), Sep. 4, 1989, abstract.
Davies, C. N. et al. (May 1972). "Breathing of Half-Micron Aerosols," Journal of Applied Physiology. 32(5):591-600.
Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.
Finlay, W. H. (2001). "The Mechanics of Inhaled Pharmaceutical Aerosols", Academic Press: San Diego Formula 2.39. pp. 3-14 (Table of Contents). pp. v-viii.
Gonda, I. (1991). "Particle Deposition in the Human Respiratory Tract,"Chapter 176, The Lung: Scientific Foundations. Crystal R.G. and West, J.B. (eds.), Raven Publishers, New York. pp. 2289-2294.
Hatsukami D., et al. (May 1990) "A Method for Delivery of Precise Doses of Smoked Cocaine-Base to Human." Pharmacology Biochemistry & Behavior. 36(1):1-7.
Heyder, J. et al. (1986). "Deposition of Particles in the Human Respiratory Tract in the Size Range 0.005-15 μm," J. Aerosol Sci. 17(5):811-822.
Huizer, H. (1987). "Analytical Studies on Illicit Heron. V. Efficacy of Volitization During Heroin Smoking." Pharmaceutisch Weekblad Scientific Edition. 9(4):203-211.
Hurt, R. D., MD and Robertson, C. R., PhD, (Oct. 1998). "Prying Open the Door to the Tobacco Industry's Secrets About Nicotine: The Minnesota Tobacco Trial," JAMA 280(13):1173-1181.
Lichtman, A. H. et al. (1996). "Inhalation Exposure to Volatilized Opioids Produces Antinociception in Mice," Journal of Pharmacology and Experimental Therapeutics. 279(1):69-76 XP-001118649.
Martin, B. R. and Lue, L. P. (May/Jun. 1989). "Pyrolysis and Volatilization of Cocaine," Journal of Analytical Toxicology 13:158-162.
Mattox, A.J. and Carroll, M.E. (1996). "Smoked Heroin Self-Administration in Rhesus Monkeys," Psychopharmacology 125:195-201.
Meng, Y. et al. (1997). "Inhalation Studies with Drugs of Abuse", NIDA Research Monogragh 173:201-224.
Meng, Y., et al. (1999). "Pharmacological effects of methamphetamine and other stimulants via inhalation exposure," Drug and Alcohol Dependence. 53:111-120.
Pankow, J. (Mar. 2000). ACS Conference-San Francisco-Mar. 26, 2000. Chemistry of Tobacco Smoke. pp. 1-8.
Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.
Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.
Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.
Vapotronics, Inc. (1998) located at http://www.vapotronics.com.au/banner.htm., 11 pages, (visited on Jun. 5, 2000).
Vaughan, N.P. (1990). "The Generation of Monodisperse Fibres of Caffeine" J. Aerosol Sci. 21(3): 453-462.
Ward, M. E. MD, et al. (Dec. 1997). "Morphine Pharmacokinetics after Pulmonary Administration from a Novel Aerosol Delivery System," Clinical Pharmocology & Therapeutics 62(6):596-609.
Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.
Wood, R.W. et al. (1996). "Methylecgonidine Coats the Crack Particle" Pharmacology Biochemistry & Behavior. 53(1):57-66.

* cited by examiner

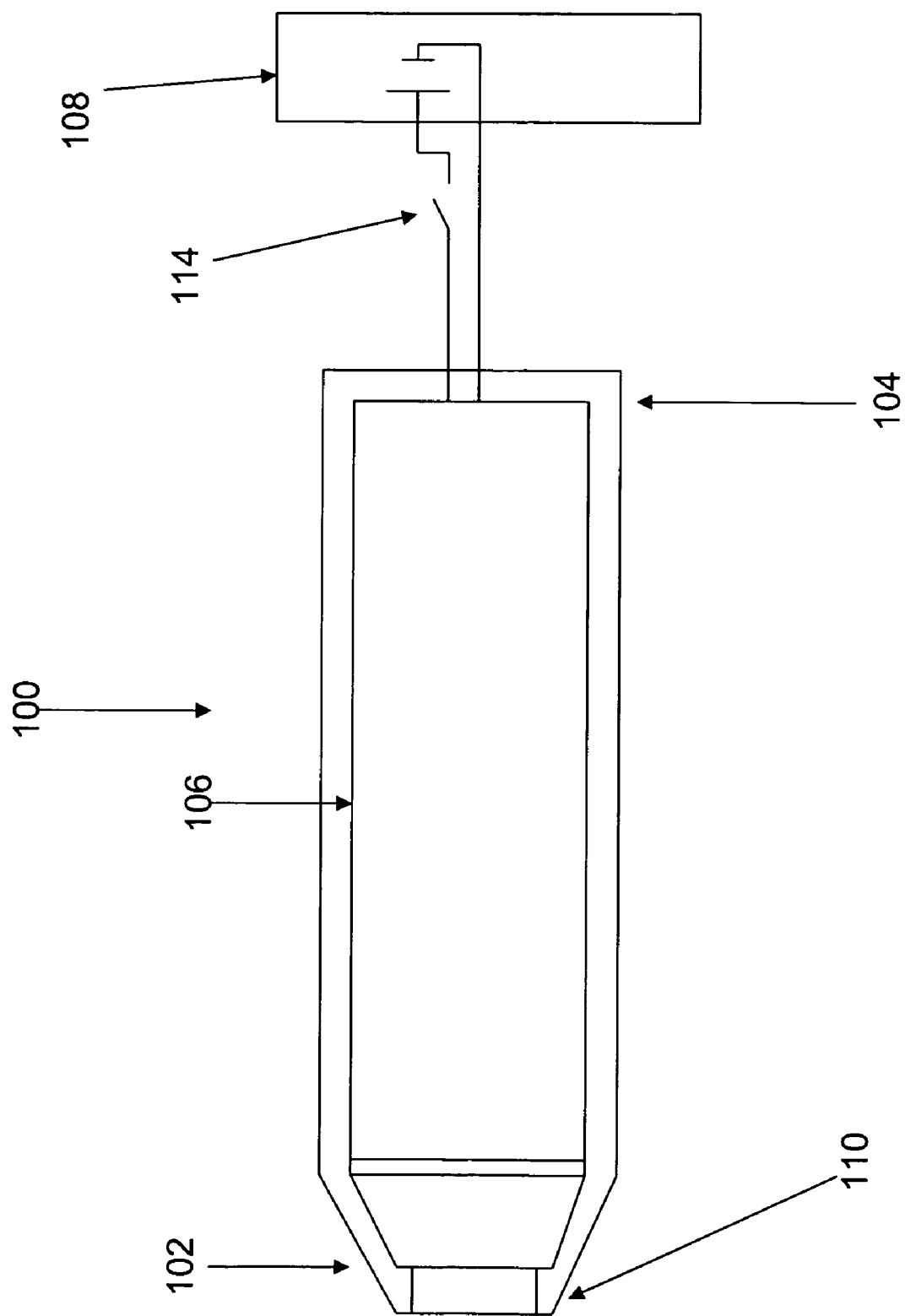

_US 7,488,469 B2_

DELIVERY OF CAFFEINE THROUGH AN INHALATION ROUTE

CROSS-REFERENCE TO RELATED APPLICATIONS

This application is a continuation of Ser. No. 10/302,010, now U.S. Pat. No. 7,078,016 entitled "Delivery of Caffeine Through An Inhalation Route" filed Nov. 21, 2002, Joshua D. Rabinowitz, which claims priority to U.S. provisional application Ser. No. 60/332,279 entitled "Delivery of Caffeine through an Inhalation Route," filed Nov. 21, 2001, Joshua D. Rabinowitz, the entire disclosures of which is hereby incorporated by reference.

FIELD OF THE INVENTION

The present invention relates to the delivery of caffeine through an inhalation route. Specifically, it relates to aerosols containing caffeine that are used in inhalation therapy.

BACKGROUND OF THE INVENTION

Caffeine is the most commonly used drug in the world. In moderate doses (75-150 mg), it elevates neural activity in many parts of the brain, postpones fatigue, and enhances performance of simple intellectual tasks and physical work that involves endurance. The most common therapeutic use of caffeine is to relieve pain, especially headache pain, although it is also a mild diuretic and a respiratory stimulant.

Typically, caffeine is administered either orally or intravenously. These delivery methods have a number of limitations. Peak plasma concentrations following oral administration are generally not reached until 50 to 75 minutes. Intravenous injection, while rapidly delivering the drug, involves the discomfort and risk of infection associated with catheterization or injection.

It is desirable to provide a new route of administration for caffeine that allows for the rapid acquisition of peak plasma concentrations without the disadvantages of catheterization or injection. The provision of such a route is an object of the present invention.

SUMMARY OF THE INVENTION

The present invention relates to the delivery of caffeine through an inhalation route. Specifically, it relates to aerosols containing caffeine that are used in inhalation therapy.

In a composition aspect of the present invention, the aerosol comprises particles comprising at least 5 percent by weight of caffeine. Preferably, the particles comprise at least 10 percent by weight of caffeine. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of caffeine.

Typically, the aerosol particles comprise less than 10 percent by weight of caffeine degradation products. Preferably, the particles comprise less than 5 percent by weight of caffeine degradation products. More preferably, the particles comprise less than 2.5, 1, 0.5, 0.1 or 0.03 percent by weight of caffeine degradation products.

Typically, the aerosol has an inhalable aerosol drug mass density of between 1 mg/L and 100 mg/L. Preferably, the aerosol has an inhalable aerosol drug mass density of between 2 mg/L and 60 mg/L. More preferably, the aerosol has an inhalable aerosol drug mass density of between 3 mg/L and 30 mg/L.

Typically, the aerosol has an inhalable aerosol particle density greater than $10^6$ particles/mL. Preferably, the aerosol has an inhalable aerosol particle density greater than $10^7$ particles/mL. More preferably, the aerosol has an inhalable aerosol particle density greater than $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the aerosol is formed by heating a composition containing caffeine to form a vapor and subsequently allowing the vapor to condense into an aerosol.

In a method aspect of the present invention, caffeine is delivered to a mammal through an inhalation route. The method comprises: a) heating a composition, wherein the composition comprises at least 5 percent by weight of caffeine; and, b) allowing the vapor to cool, thereby forming a condensation aerosol comprising particles, which is inhaled by the mammal. Preferably, the composition that is heated comprises at least 10 percent by weight of caffeine. More preferably, the composition comprises 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of caffeine.

Typically, the delivered aerosol particles comprise at least 5 percent by weight of caffeine. Preferably, the particles comprise at least 10 percent by weight of caffeine. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of caffeine.

Typically, the delivered aerosol particles comprise less than 10 percent by weight of caffeine degradation products. Preferably, the particles comprise less than 5 percent by weight of caffeine degradation products. More preferably, the particles comprise less than 2.5, 1, 0.5, 0.1 or 0.03 percent by weight of caffeine degradation products.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the delivered aerosol has an inhalable aerosol drug mass density of between 1 mg/L and 100 mg/L. Preferably, the aerosol has an inhalable aerosol drug mass density of between 2 mg/L and 60 mg/L. More preferably, the aerosol has an inhalable aerosol drug mass density of between 3 mg/L and 30 mg/L.

Typically, the delivered aerosol has an inhalable aerosol particle density greater than $10^6$ particles/mL. Preferably, the aerosol has an inhalable aerosol particle density greater than $10^7$ particles/mL. More preferably, the aerosol has an inhalable aerosol particle density greater than $10^8$ particles/mL.

Typically, the rate of inhalable aerosol particle formation of the delivered condensation aerosol is greater than $10^8$ particles per second. Preferably, the aerosol is formed at a rate greater than $10^9$ inhalable particles per second or $10^{10}$ inhalable particles per second.

Typically, the delivered aerosol is formed at a rate greater than 1 mg/second. Preferably, the aerosol is formed at a rate greater than 5 mg/second. More preferably, the aerosol is formed at a rate greater than 20 mg/second.

Typically, the condensation aerosol delivers between 1 mg and 100 mg of caffeine to the mammal in a single inspiration. Preferably, between 2 mg and 60 mg of caffeine are delivered to the mammal in a single inspiration. More preferably, between 3 mg and 30 mg of caffeine are delivered to the mammal in a single inspiration.

Typically, the delivered condensation aerosol results in a peak plasma concentration of caffeine in the mammal in less than 1 h. Preferably, the peak plasma concentration is reached in less than 0.5 h. More preferably, the peak plasma concentration is reached in less than 0.2, 0.1, 0.05, 0.02 or 0.01 h.

In a kit aspect of the present invention, a kit for delivering caffeine through an inhalation route to a mammal is provided which comprises: a) a composition comprising at least 5 percent by weight of caffeine; and, b) a device that forms a caffeine containing aerosol from the composition, for inhalation by the mammal. Preferably, the composition comprises at least 10 percent by weight of caffeine. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of caffeine.

Typically, the device contained in the kit comprises: a) an element for heating the caffeine composition to form a vapor; b) an element allowing the vapor to cool to form an aerosol; and, c) an element permitting the mammal to inhale the aerosol.

BRIEF DESCRIPTION OF THE FIGURE

FIG. 1 shows a device used to deliver caffeine containing aerosols to a mammal through an inhalation route.

DETAILED DESCRIPTION OF THE INVENTION

Definitions

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Aerosol drug mass density" refers to the mass of caffeine per unit volume of aerosol.

"Aerosol mass density" refers to the mass of particulate matter per unit volume of aerosol.

"Aerosol particle density" refers to the number of particles per unit volume of aerosol.

"Condensation aerosol" refers to an aerosol formed by vaporization of a substance followed by condensation of the substance into an aerosol.

"Caffeine" refers to 3,7-dihydro-1,3,7-trimethyl-1H-purine-2,6-dione, which is a free base.

"Caffeine" degradation product refers to a compound resulting from a chemical modification of caffeine. The modification, for example, can be the result of a thermally or photochemically induced reaction. Such reactions include, without limitation, oxidation and hydrolysis.

"Inhalable aerosol drug mass density" refers to the aerosol drug mass density produced by an inhalation device and delivered into a typical patient tidal volume.

"Inhalable aerosol mass density" refers to the aerosol mass density produced by an inhalation device and delivered into a typical patient tidal volume.

"Inhalable aerosol particle density" refers to the aerosol particle density of particles of size between 100 nm and 5 microns produced by an inhalation device and delivered into a typical patient tidal volume.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Rate of aerosol formation" refers to the mass of aerosolized particulate matter produced by an inhalation device per unit time.

"Rate of inhalable aerosol particle formation" refers to the number of particles of size between 100 nm and 5 microns produced by an inhalation device per unit time.

"Rate of drug aerosol formation" refers to the mass of aerosolized caffeine produced by an inhalation device per unit time.

"Settling velocity" refers to the terminal velocity of an aerosol particle undergoing gravitational settling in air.

"Typical patient tidal volume" refers to 1 L for an adult patient and 15 mL/kg for a pediatric patient.

"Vapor" refers to a gas, and "vapor phase" refers to a gas phase. The term "thermal vapor" refers to a vapor phase, aerosol, or mixture of aerosol-vapor phases, formed preferably by heating.

Formation of Caffeine Containing Aerosols

Any suitable method is used to form the aerosols of the present invention. A preferred method, however, involves heating a composition comprising caffeine to produce a vapor, followed by cooling of the vapor such that it condenses to provide a caffeine comprising aerosol (condensation aerosol). The composition is heated in one of two forms: as pure active compound (i.e., pure caffeine); or, as a mixture of active compound and a pharmaceutically acceptable excipient. Typically, the composition is heated on a solid support.

Pharmaceutically acceptable excipients are either volatile or nonvolatile. Volatile excipients, when heated, are concurrently volatilized, aerosolized and inhaled with caffeine. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid supports on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, solid supports provide a large surface to volume ratio (e.g., greater than 100 per meter) and a large surface to mass ratio (e.g., greater than 1 $cm^2$ per gram).

A solid support of one shape can also be transformed into another shape with different properties. For example, a flat sheet of 0.25 mm thickness has a surface to volume ratio of approximately 8000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the solid supports. Classes of such materials include, without limitation, metals, inorganic materials, carbonaceous materials and polymers. The following are examples of the material classes: aluminum, silver, gold, stainless steel, copper and tungsten; silica, glass, silicon and alumina; graphite, porous carbons, carbon yams and carbon felts; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 $m^2/g$ from Aldrich, St. Louis, Mo.) and a silicon wafer as used in the semiconductor industry. Carbon yams and felts are available from American Kynol, Inc., New York, N.Y. Chromatography resins such as octadecycl silane chemically bonded to porous silica are exemplary coated variants of silica.

The heating of the caffeine compositions is performed using any suitable method. Examples of methods by which heat can be generated include the following: passage of current through an electrical resistance element; absorption of electromagnetic radiation, such as microwave or laser light; and, exothermic chemical reactions, such as exothermic solvation, hydration of pyrophoric materials and oxidation of combustible materials.

Delivery of Caffeine Containing Aerosols

Caffeine containing aerosols of the present invention are delivered to a mammal using an inhalation device. Where the aerosol is a condensation aerosol, the device has at least three elements: an element for heating a caffeine containing composition to form a vapor; an element allowing the vapor to cool, thereby providing a condensation aerosol; and, an element permitting the mammal to inhale the aerosol. Various suitable heating methods are described above. The element that allows cooling is, in it simplest form, an inert passageway linking the heating means to the inhalation means. The element permitting inhalation is an aerosol exit portal that forms a connection between the cooling element and the mammal's respiratory system.

One device used to deliver caffeine containing aerosol is described in reference to FIG. 1. Delivery device 100 has a proximal end 102 and a distal end 104, a heating module 106, a power source 108, and a mouthpiece 110. A caffeine composition is deposited on a surface 112 of heating module 106. Upon activation of a user activated switch 114, power source 108 initiates heating of heating module 106 (e.g. through ignition of combustible fuel or passage of current through a resistive heating element). The caffeine composition volatilizes due to the heating of heating module 106 and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by the mammal.

Devices, if desired, contain a variety of components to facilitate the delivery of caffeine containing aerosols. For instance, the device may include any component known in the art to control the timing of drug aerosolization relative to inhalation (e.g., breath-actuation), to provide feedback to patients on the rate and/or volume of inhalation, to prevent excessive use (i.e., "lock-out" feature), to prevent use by unauthorized individuals, and/or to record dosing histories.

Dosage of Caffeine Containing Aerosols

For analgesis effect or the relief of migraine headache, caffeine is given orally at doses between 30 mg and 100 mg, generally in combination with another active compound (e.g., aspirin or ergotamine, respectively). As an aerosol, between 3 and 30 mg of caffeine is generally provided per inspiration for these indications. A typical dosage of a caffeine aerosol is either administered as a single inhalation or as a series of inhalations taken within an hour or less (dosage equals sum of inhaled amounts). Where the drug is administered as a series of inhalations, a different amount may be delivered in each inhalation. The dosage amount of caffeine in aerosol form is generally no greater than twice the standard dose of the drug given through other methods.

One can determine the appropriate dose of a caffeine containing aerosol to treat a particular condition using methods such as animal experiments and a dose-finding (Phase I/II) clinical trial. One animal experiment involves measuring plasma concentrations of drug in an animal after its exposure to the aerosol. Mammals such as dogs or primates are typically used in such studies, since their respiratory systems are similar to that of a human. Initial dose levels for testing in humans are generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

Analysis of Caffeine Containing Aerosols

Purity of a caffeine containing aerosol is determined using a number of methods, examples of which are described in Sekine et al., *Journal of Forensic Science* 32:1271-1280 (1987) and Martin et al., *Journal of Analytic Toxicology* 13:158-162 (1989). One method involves forming the aerosol in a device through which a gas flow (e.g., air flow) is maintained, generally at a rate between 0.4 and 60 L/min. The gas flow carries the aerosol into one or more traps. After isolation from the trap, the aerosol is subjected to an analytical technique, such as gas or liquid chromatography, that permits a determination of composition purity.

A variety of different traps are used for aerosol collection. The following list contains examples of such traps: filters; glass wool; impingers; solvent traps, such as dry ice-cooled ethanol, methanol, acetone and dichloromethane traps at various pH values; syringes that sample the aerosol; empty, low-pressure (e.g., vacuum) containers into which the aerosol is drawn; and, empty containers that fully surround and enclose the aerosol generating device. Where a solid such as glass wool is used, it is typically extracted with a solvent such as ethanol. The solvent extract is subjected to analysis rather than the solid (i.e., glass wool) itself. Where a syringe or container is used, the container is similarly extracted with a solvent.

The gas or liquid chromatograph discussed above contains a detection system (i.e., detector). Such detection systems are well known in the art and include, for example, flame ionization, photon absorption and mass spectrometry detectors. An advantage of a mass spectrometry detector is that it can be used to determine the structure of caffeine degradation products.

Particle size distribution of a caffeine containing aerosol is determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density is determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug mass density is determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of active drug compound collected in the chamber is determined by extracting the chamber, conducting chromatographic analysis of the extract and comparing the results of the chromatographic analysis to those of a standard containing known amounts of drug.

Inhalable aerosol particle density is determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size may be determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi * D^3 * \phi/6$, where D is a typical particle diameter in the size range (generally, the mean of the boundary MMADs defining the size range) in microns, $\phi$ is the particle density (in g/mL) and mass is given in units of picograms ($g^{-12}$).

Rate of inhalable aerosol particle formation is determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation is determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation is determined, for example, by delivering a caffeine containing aerosol into a confined chamber via an inhalation device over a set period of time (e.g., 3 s). Where the aerosol is pure caffeine, the amount of drug collected in the chamber is measured as described above. The rate of drug aerosol formation is equal to the amount of caffeine collected in the chamber divided by the duration of the collection time. Where the caffeine containing aerosol comprises a pharmaceutically acceptable excipient, multiplying the rate of aerosol formation by the percentage of caffeine in the aerosol provides the rate of drug aerosol formation.

Utility of Caffeine Containing Aerosols

The following are typical uses for caffeine aerosols of the present invention: respiratory stimulation; acute treatment of fatigue; enhancement of alertness; treatment of narcolepsy; induction of a positive state of mind; analgesia; treatment of nicotine craving; treatment of cocaine and other elicit drug craving; and, treatment of headache, including without limitation, tension headache, migraine headache and headache due to leakage of cerebrospinal fluid.

The following examples are meant to illustrate, rather than limit, the present invention.

Caffeine is commercially available from Sigma.

EXAMPLE 1

Volatilization of Caffeine

A furnace tube was connected to a vacuum outlet. In between the tube and the outlet was placed a glass wool plug. The furnace tube was preheated to 300° C. Caffeine (82 mg) was added to the preheated tube, and an air flow rate of 2 L/min was applied using the vacuum. After 2 min, the furnace tube was allowed to cool. The walls of the tube outside of the heating zone and the glass wool were extracted with solvent. Analysis of the extract showed that approximately 40% of the caffeine had volatilized at a purity level >99%.

EXAMPLE 2

Particle Size of Caffeine Aerosol

An Andersen Eight Stage Non-viable Cascade Impactor (Andersen Instruments, Smyrna, Ga.) was linked to a furnace tube by a mock throat (USP throat, Andersen Instruments, Smyrna, Ga.) for cascade impaction studies. The furnace tube was preheated to 350° C. To the preheated tube was added 100 mg caffeine. After 15 s, an air flow of 28 L/min was applied for 2 min. The tube was allowed to cool, and the results from the cascade impactor were analyzed (see Table 1). MMAD of the collected aerosol was 1.1 microns with a geometric standard deviation of 3.

TABLE 1

Determination of the particle size of a caffeine condensation aerosol by cascade impaction using an Andersen 8-stage non-viable cascade impactor.

| Stage | Particle size range (microns) | Average particle size (microns) | Mass collected (mg) |
| --- | --- | --- | --- |
| 0 | 9.0-10.0 | 9.5 | 1.2 |
| 1 | 5.8-9.0 | 7.4 | (0.6) |
| 2 | 4.7-5.8 | 5.25 | 3.0 |
| 3 | 3.3-4.7 | 4.0 | 5.1 |
| 4 | 2.1-3.3 | 2.7 | 6.7 |
| 5 | 1.1-2.1 | 1.6 | 6.4 |
| 6 | 0.7-1.1 | 0.9 | 5.2 |
| 7 | 0.4-0.7 | 0.55 | 5.2 |
| 8 | 0-0.4 | 0.2 | 2.6 |

The invention claimed is:

1. A condensation aerosol for delivery of caffeine formed by heating a composition containing caffeine coated on a solid support to form a vapor and condensing the vapor to form a condensation aerosol comprising particles, wherein the particles comprise at least 10 percent by weight of caffeine and less than 5 percent by weight of caffeine degradation products, and the condensation aerosol has an MMAD of less than 5 microns.

2. The condensation aerosol according to claim 1, wherein the condensation aerosol has an MMAD of less than 3 microns.

3. The condensation aerosol according to claim 1 or claim 2, wherein the condensation aerosol has an MMAD of less than 2 microns.

4. A method of forming a caffeine containing aerosol comprising:
(a) heating a composition containing caffeine coated on a solid support to form a vapor; and
(b) condensing the vapor to form a condensation aerosol comprising particles,
wherein the particles comprise less than 5 percent by weight of caffeine degradation products, and the condensation aerosol has an MMAD of less than 5 microns.

5. The method according to claim 4, wherein the condensation aerosol has an MMAD of less than 3 microns.

6. The method according to claim 5, wherein the coated composition comprises at least 10 percent by weight of caffeine.

7. A method of forming a caffeine containing aerosol comprising:
(a) heating a composition containing caffeine and a pharmaceutically acceptable excipient coated on a solid support to form a vapor; and
(b) condensing the vapor to form a condensation aerosol comprising particles,
wherein the particles comprise at least 10 percent by weight of caffeine and less than 5 percent by weight of caffeine degradation products and the condensation aerosol has an MMAD of less than 5 microns.

8. The method according to claim 7, wherein the condensation aerosol has an MMAD of less than 3 microns.

9. The method according to claim 8, wherein the coated composition comprises at least 10 percent by weight of caffeine.

10. The method according to claim 8, wherein the condensing comprises allowing the vapor to cool.

11. The condensation aerosol according to claim 2, wherein the condensing comprises allowing the vapor to cool.

12. The method according to claim 5, wherein the condensing comprises allowing the vapor to cool.

13. A method of forming a caffeine containing aerosol comprising:
(a) heating a composition containing caffeine coated on a solid support to form a vapor, and
(b) condensing the vapor to form a condensation aerosol comprising particles, wherein the condensation aerosol is formed at a rate greater than 1 mg/second, and
wherein the particles comprise at least 10 percent by weight of caffeine and less than 5 percent by weight of caffeine degradation products, and the condensation aerosol has an MMAD less than 5 microns.

14. The method according to claim 13, wherein the condensation aerosol has an MMAD of less than 3 microns.

15. The method according to claim 14, wherein the condensation aerosol is formed at a rate greater than 5 mg/second.

16. The method according to claim 15, wherein the condensation aerosol is formed at a rate greater than 20 mg/second.

17. The method according to claim 13, wherein the condensing comprises allowing the vapor to cool.

* * * * *